United States Patent [19]

Fischer

[11] Patent Number: 4,954,105
[45] Date of Patent: Sep. 4, 1990

[54] REPLACEMENT CONNECTOR FOR IMPLANTED LEADS

[75] Inventor: Elmar R. Fischer, Lake Jackson, Tex.
[73] Assignee: Intermedics, Inc., Angleton, Tex.
[21] Appl. No.: 458,175
[22] Filed: Dec. 28, 1989
[51] Int. Cl.$^5$ ............................................. H01R 11/11
[52] U.S. Cl. ................................... 439/864; 128/786; 439/909
[58] Field of Search ................ 439/864, 909; 174/845; 128/419 P, 784–786

Primary Examiner—Gary F. Paumen
Attorney, Agent, or Firm—John R. Merkling

[57] ABSTRACT

A replacement connector for implanted leads. The proximal end of the implanted lead is cut away and discarded. A slip-on seal is placed on the remaining end of the lead. The replacement connector is connected to the implanted lead using an eccentric locking mechanism both to secure the implanted lead and the replacement connector together and to achieve a positive electrical connection. A boot mates with the slip-on seal to protect the connection from body fluids.

16 Claims, 4 Drawing Sheets

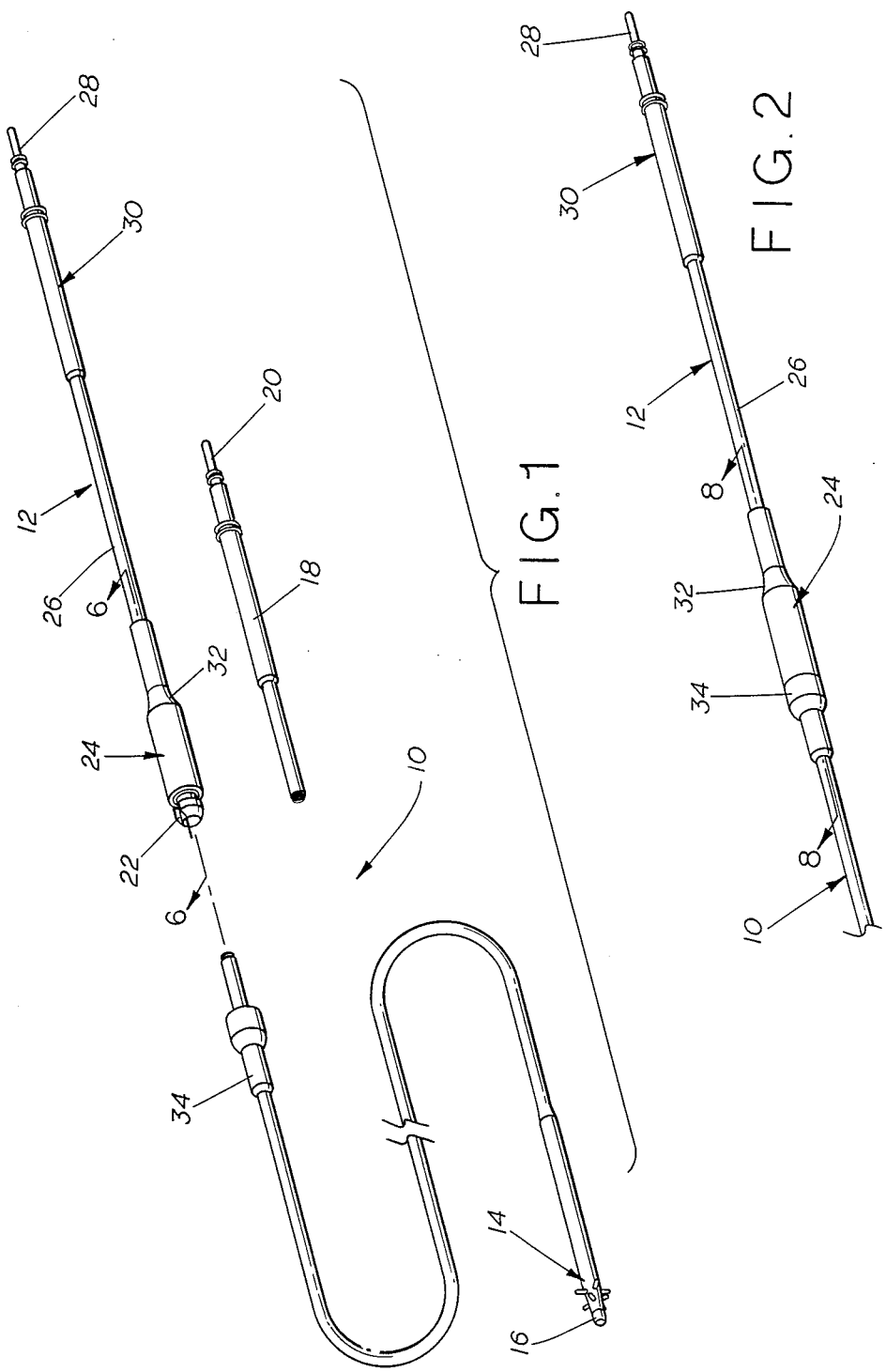

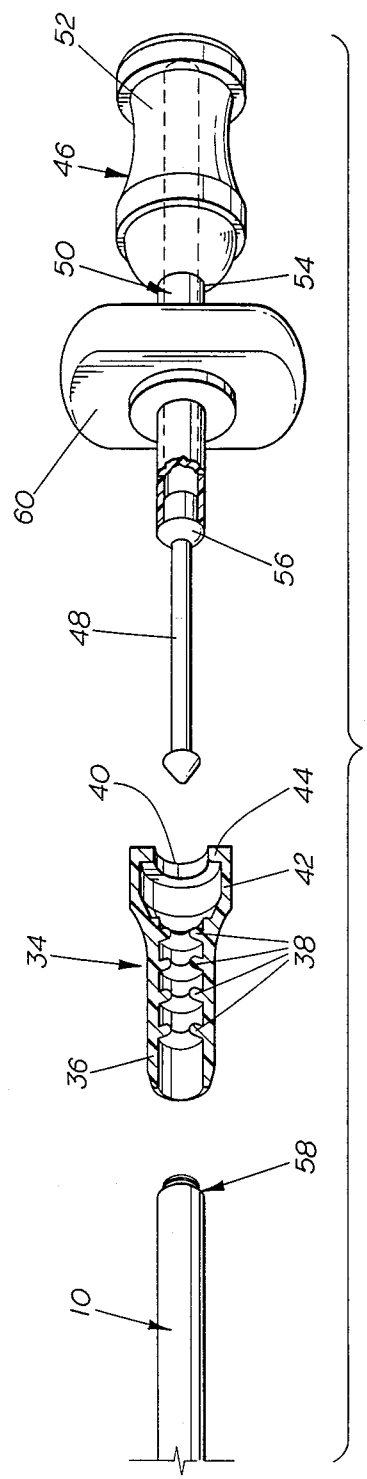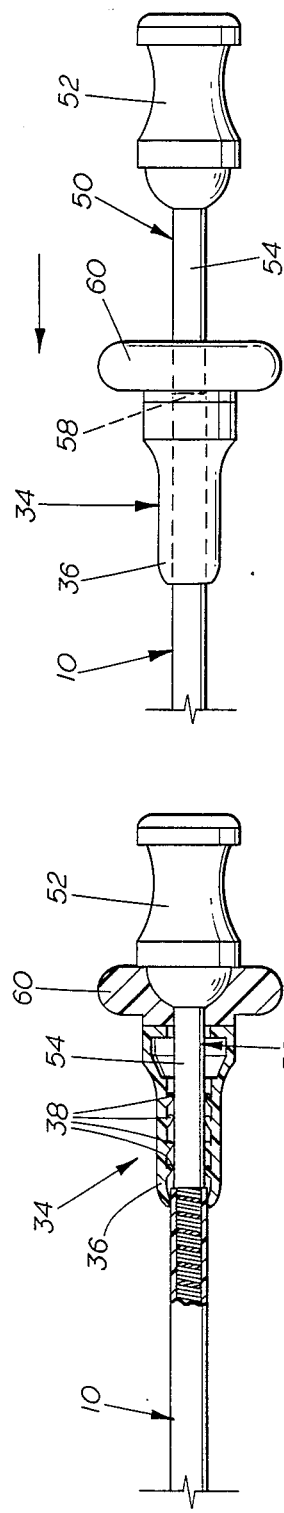

REPLACEMENT CONNECTOR FOR IMPLANTED LEADS

BACKGROUND OF THE INVENTION

1. Field of the Invention

The present invention relates generally to cardiac stimulation, and more particularly to implantable leads which simulate or sense electrical activity of the heart. The invention provides a replacement connector which can be connected to an implanted lead in place of a proximal end of the lead.

2. Prior Art

There are generally two types of body implantable leads used with cardiac pacemakers—one which requires surgery to expose the myocardia tissue to which an electrode is affixed and another which is inserted through a body vessel, such as a vein, into the heart where a electrode contacts the endocardial tissue. In the later type, the endocardial lead is often secured to the heart through an endothelial lining by a sharpened helix affixed to a distal end of the lead. When the end of the lead contacts the lining of the heart at a desired location, the lead may be secured in place by rotating the lead, thus screwing the helix into the heart tissue.

When an implantable lead is affixed to the heart tissue, it initially exhibits a certain impedance associated with the character and composition of the lead, the location and quality of fixation, and other factors. Over time, the heart tissue reacts to the presence of the foreign body, forming a fibrosis in the tissue near the electrode. Shortly after implantation, therefore, the impedance associated with an implanted electrode rises from an initial value to a peak value. Thereafter, the impedance associated with the electrode again falls to a lower value as the fibrosis stabilizes and eventually a relatively stable, long-term impedance value is attained.

This phenomenon is well known. One consequence of this condition is that initial settings for implanted pacers must be higher than the measured impedance at the time of implantation. An attending physician would expect the impedance to rise over time and would, therefore, adjust the pacer to produce pulses of higher energy in order to insure an appropriate response in the heart during the period of highest impedance. Frequently, the pacer is not adjusted after the impedance falls to its stable long-term value, resulting in an unnecessary use of pacer power. Higher power consumption results in more rapid battery depletion, which eventually requires that the pacer itself be replaced sooner than would be otherwise necessary. It is desireable, therefore, for a physician to be able to use a lead which has already stabilized to its long-term impedance, whenever the pacer is replaced. Use of a stabilized lead can permit the attending physician to more accurately adjust both sensing and stimulating parameters to conserve energy and to assure reliable long-term performance of the implanted pacer.

The replacement pacer, however, may not be the same type as the original pacer. Over the expected life of the pacer, on the order of ten years, it is to be expected that technology and manufacturing will have changed. New options in pacing technology have become and will become available. Moreover, the patient's condition may have changed, making it desireable to incorporate different features in the replacement pacer, which were not necessary in the original pacer. Because it is quite likely that the electrical connections on the replacement pacer would not be identical to the original pacer, it is desireable to provide a means whereby a distal end of the implanted lead could be left in its stabilized condition near or on the heart tissue, while the proximal end of the lead is replaced with an end compatible with the replacement pacer.

SUMMARY OF THE INVENTION

The present invention provides a replacement connector for implanted leads. When a implanted lead is used with a replacement pacer, the proximal end of the implanted lead is cut away and discarded. A slip-on seal is placed on the remaining end of the lead. The replacement connector is connected to the implanted lead using an eccentric locking mechanism both to secure the implanted lead and the replacement connector together and to achieve a positive electrical connection. A boot mates with the slip-on seal to protect the connection from body fluids.

With the foregoing in mind, it is a principal object of the present invention to provide a replacement connector for implanted leads.

A further object of the invention is to provide a replacement connector which can be secured to an implanted lead by a reliable mechanical and electrical connection.

Another important object of the present invention is to provide a replacement connector which can be sealed against body fluids.

Another object of the invention is to provide a means for connecting an implanted lead and a replacement connector which can be engaged with a minimum of manipulation.

These and other objects and features of the present invention will be apparent from the detailed description taken with reference to the accompanying drawing.

BRIEF DESCRIPTION OF DRAWINGS

FIG. 1 is a prospective view of an implantable endocardial lead with a replacement pacer connector accoording to the present invention;

FIG. 2 is prospective view of a proximal part of the implanted lead with the replacement connector attached thereto;

FIG. 3 is a sectional view of a slip-on seal and installation jig;

FIG. 4 is a sectional view of the slip-on seal and the installation jig showing the installation procedure;

FIG. 5 is a side view of the slip-on seal and jig;

DETAILED DESCRIPTION OF THE PREFERRED EMBODIMENT

Figure 6:
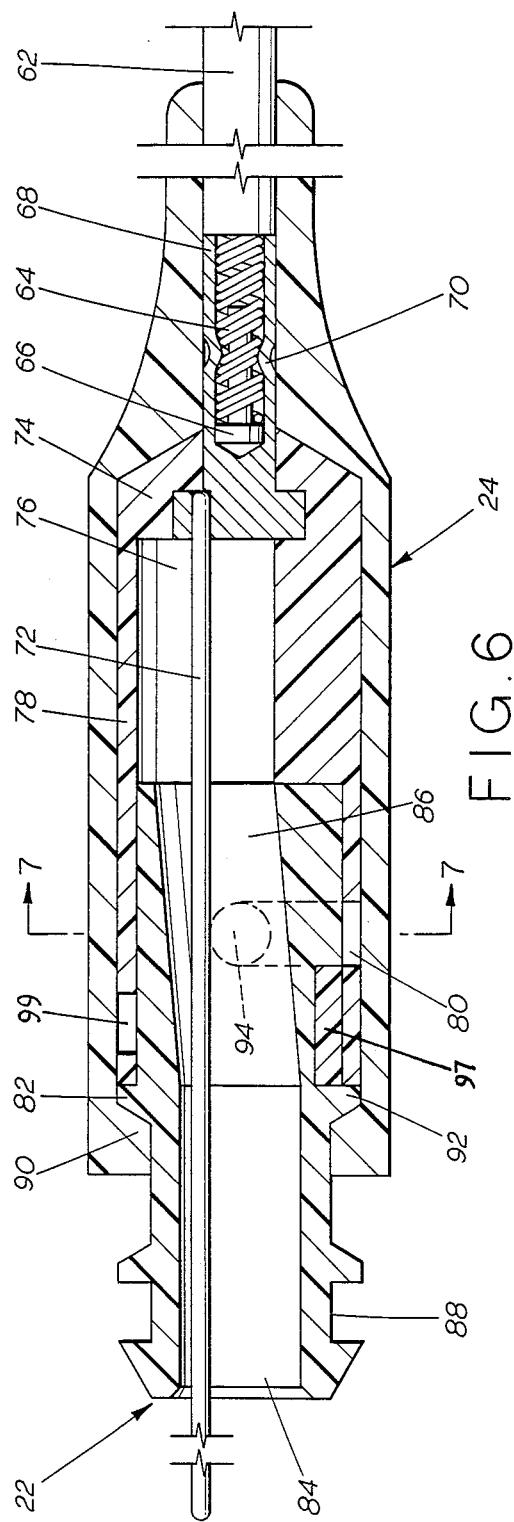
FIG. 6 is a sectional view of a distal end of the replacement connector taken along line 6—6 of FIG. 1.
Figure 9:
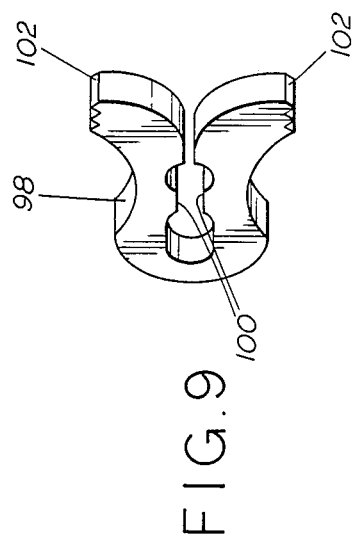
FIG. 9 is a prospecive view of a wrench for use with the present invention.

Reference is now made to the drawings, wherein like numerals designate like parts throughout. FIG. 1 shows an implanted endocardial lead generally designated 10 and a replacement connector generally designated 12. In accordance with the prior art, the implanted lead comprises a distal end 14 with a tip electrode 16 and a proximal end 18 with a connector 20. The replacement connector 12, according to the present invention, comprises a connector housing 22 at a connector distal end 24, a lead portion 26 and a connection 28 at a proximal end 30 of the replacement connector 12. An elastomeric boot 32 encloses most of the housing 22. The boot 32 mates with a slip-on seal 34 to inhibit body fluid from entering the housing 22. The slip-on seal 34 rides on a portion of the implanted lead 10, as will be more fully described below.

To install the replacement connector 12, an attending physician would cut the implanted lead 10 near the proximal end 18 with wire cutters or a similar tool and would discard the proximal end 18. The slip-on seal 34 must then be placed on the implanted lead 10. As seen FIG. 3, the slip-on seal 34 comprises an elastomeric, preferably silicone, tube 36 with a plurality of internal sealing fins 38. The sealing fins 38 are circumferential around the interior of the tube 36 and are inclined toward a proximal end 40 of the seal 34. Because of this configuration, it is relatively easier to slide the seal 34 along the implanted lead 10 toward the distal end 14 thereof. When the seal 34 is moved toward the proximal end of the lead 10, the fins 38 tend both to resist the motion and simultaneously to form a tighter seal on the lead 10.

The seal 34 further comprises a larger tube 42 at the distal end 40 of the seal 34 for engaging the housing 22 and boot 24 as more fully explained below. A lip 44 is provided at the distal end 40 of the seal 34 for locking with the housing 22 and the boot 24.

In order to provide reliable sealing, the slip-on seal 34 is provided with an installation jig 46. A handle 52 is attached to a proximal end 54 of a shaft 50 and a break-away pin 48 is attached to a distal end 56 of the shaft 50. In the preferred embodiment, the slip-on seal 34 rides on the break-away pin 48 until the replacement connector 12 is to be installed. The break-away pin 48 has a relative small diameter so that the tube 36 and fins 38 of the seal 34 are not distended prior to being placed on the implanted lead 10. Silicone and other elastomeric substances tend to deform permanently if placed under stress for an extended time. Just before installation, therefore, the slip-on seal 34 should be pushed off of the detachable pin 48 and onto a shaft 50 of the jig 46. The shaft 50 has an outside diameter roughly corresponding to the expected outside diameter of the implanted lead 10. With the slip-on seal 34 on the shank 50, the break-away pin 48 can be removed from the jig 46. The distal end 56 of the shank 50 is placed against a severed end 58 of the lead 10. The slip-on seal 34 can then be pushed onto the lead 10 using a push block 60, as shown in FIG. 4 and 5.

Figure 7:
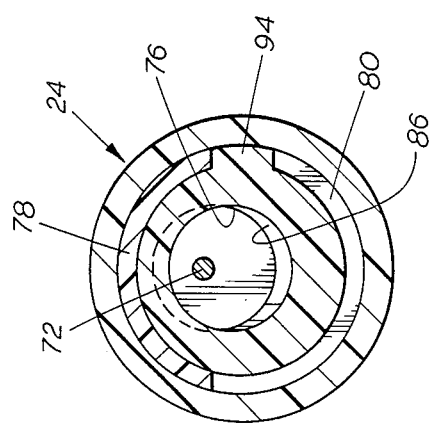
FIG. 7 is a cross-sectional view of the distal end of the replacement connector taken along line 7—7 of FIG. 6.

With the slip-on seal 34 on the implanted lead 10, the replacement connector 12 can be secured to the severed end 58 of the lead 10. The housing 22 which engages the severed end 58 will now be explained in connection with FIG. 6, 7, and 8. The lead portion 26 of the replacement connector 12 comprises a silicone sleeve 62 containing a trifilar coil conductor 64. A crimp slug 66 and a conductive body 68 make an electrical connection with the trifilar coil conductor 64 by mechanical pressure of a crimp 70. The conductive body 68 is in electrical communication with a conducting guide wire 72 which is spaced away from the longitudinal axis of the replacement connector 12, but parallel thereto. Affixed to the conducting portion 68 is a stationary housing 74 which is preferably formed of a relatively ridged plastic, such as high density polyacetate. The stationary housing 74 comprises a cylindrical chamber 76 which is coaxial with the conducting guide wire 72. The cylindrical chamber 76 has a diameter approximately equal to the outside diameter of the implanted lead 10 and is located adjacent the conducting part 68 and near the proximal end of the stationary housing 74. The distal end of the stationary housing 74 comprises a tube 78 which is concentric with the longitudinal axis of the replacement connector 12. A guide slot 80 in the tube 78 permits the housing 22 to be manipulated accurately, as will be more fully described below. A rotatable housing 82 rotatably engages the inner surface of the tube 78. The rotatable housing 82 has a coaxial bore 84 at a distal end of the rotatable housing 82. The coaxial bore 84 has an inside diameter similar to the outside diameter of the implanted lead 10. An inclined bore 86 joins with the proximal end of the coaxial bore 84 and can coincide with the cylindrical chamber 76. Wrench flats 88 at the distal end of the rotatable housing 82 permit the rotatable housing 82 to the rotated with the respect to the stationary housing 74. The elastomeric, preferably silicone, boot 24 surrounds the stationary housings 74 and the proximal end of the rotatable housing 82. A lip 90 at the distal end of the boot 24 engages a ring 92 on the rotatable housing 82 to hold the two housing 74, 82 together. A guide pin 94, attached to the rotatable housing 82 slides in the guide slot 80 and limits the rotation of the rotatable housing 82 with respect to the stationary housing 74.

Figure 8:
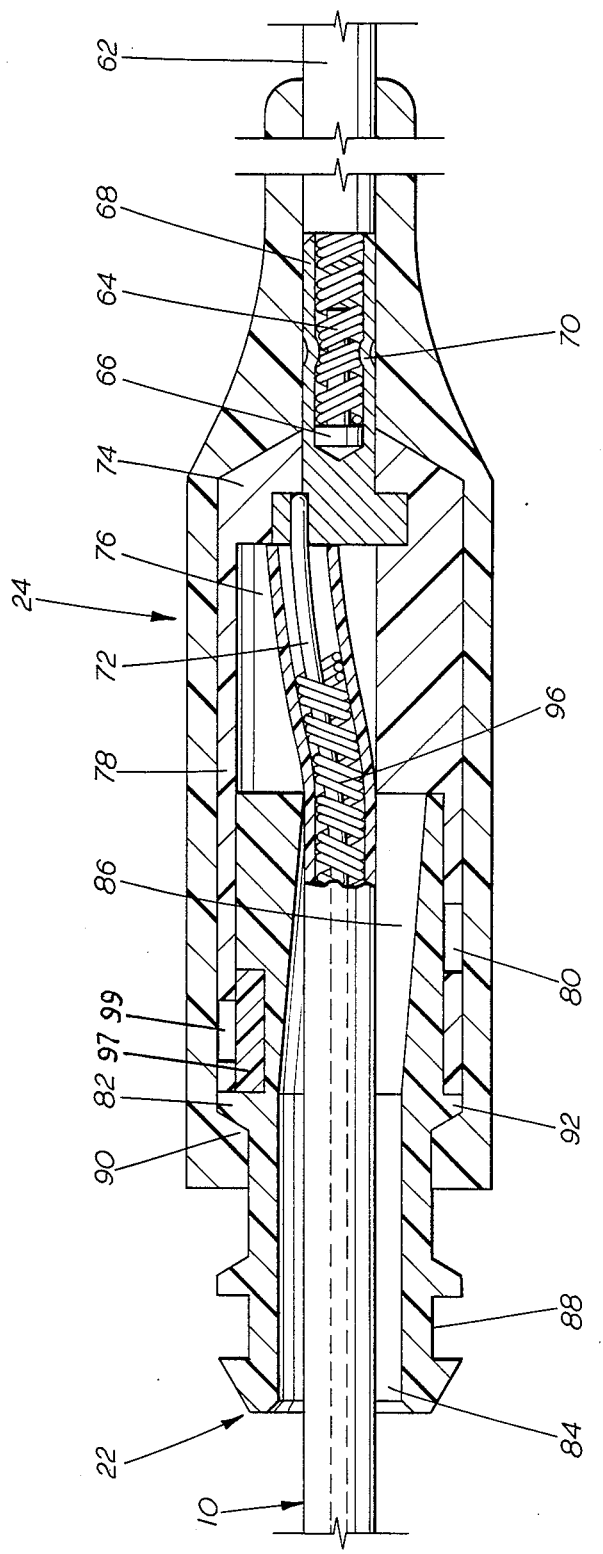
FIG. 8 is a cross-sectional view of the distal end of the replacement connector taken along line 8—8 of FIG. 2.

When the replacement connector 12 is attached to a implanted lead 10, the conducting guide wire 72 is threaded into a trifilar coil 96 in the lead 10. The severed end 58 of the lead 10 is then pushed along the conducting guide wire 72, through the coaxial bore 84 and the inclined bore 86 into the cylindrical chamber 76. The rotatable housing 82 can then be rotated with a wrench 98 so that the lead 10 is pinched between the stationary housing 74 and rotating housing 82, as shown in FIG. 8. An electrical connection is formed by mechanical contact between the trifilar connector 96 and the conducting guide wire 72, particularly at the interface between the stationary housing 74 and the rotating housing 82. To indicate that rotation has been completed, a portion of the rotating housing 82 can be replaced by a colored plug 97. When rotation is complete the colored plug can be seen through a hole 99 in the stationary housing 74. The color of the plug 97 can be seen through the translucent silicone forming the boot 24. The wrench 98 can be removed from the wrench flats 88 on the rotatable housing 82 and slip on seal 34 can be pushed over the distal end of the rotating housing 82 and against the boot 24 to form a seal which resists the intrusion of body fluids into either the implanted lead 10 or the replacement connector 12.

In the preferred embodiment, a specialized wrench is provided having flats 100 for engaging the wrench flats 88 and ridged extensions 102 which can be manipulated by an attending physician wearing surgical gloves.

The invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the meaning and range equivalency of the claims are therefore intended to be embraced therein.

What is claimed and desired to be secured by U.S. Letters Patented is:

1. A connector for replacement of a proximal end of an implanted lead, the connector comprising:
   means for making an electrical connection with an electrical conductor in a severed end of the implanted lead from which the proximal end of the implanted lead has been removed;
   means for securing a distal end of the connector to the severed end of the implanted lead;
   terminal means at a proximal end of the connector for electrical connection to a medical device; and
   conductor means electrically connecting the connection making means to the terminal means.

2. The connector according to claim 1 wherein the securing means comprises
   a stationary housing with a chamber spaced away from an axis of the stationary housing; and
   a rotatable housing in contact with the stationary housing, the rotatable housing having a bore, a proximal end of the bore being adapted to selectively coincide with a distal end of the chamber, the chamber and the bore being adapted to receive the end of the implanted lead.

3. The connector according to claim 2 wherein the bore of the rotatable housing comprises a coaxial bore at a distal end of the rotatable housing and an inclined bore communicating at its distal end with the coaxial bore and selectively communicating at its proximal end with the chamber.

4. The connector according to claim 3 wherein the securing means further comprise means for limiting the movement of the rotatable housing with respect to the stationary housing.

5. The connector according to claim 3 wherein the movement limiting means comprise a slot in the stationary housing and a pin on the rotatable housing, the pin mating with the slot and slidable therein.

6. The connector according to claim 5 wherein the chamber, the coaxial bore and the inclined bore are cyindrical.

7. The connector according to claim 6 wherein the connection making means comprises a guide wire for insertion into the severed end of the lead.

8. The connector according to claim 7 wherein the guide wire passes through the chamber, the inclined bore and the coaxial bore.

9. The connector according to claim 8 further comprising means for excluding body fluids.

10. The connector according to claim 9 wherein the excluding means comprise
    an elastomeric boot substantially enclosing the stationary housing and the rotatable housing, and
    an elastomeric seal carried on the severed end of the lead and adapted to sealingly connect with the elastomeric boot.

11. The connector according to claim 10 wherein the elastomeric seal comprises
    a tube and
    a plurality of concentric inclined fins on an inner wall of the tube.

12. A method for securing a replacement connector having a replacement proximal lead end to an implanted lead, comprising the steps of
    severing a proximal end of an implanted lead;
    making an electrical connection between the implanted lead and the replacement connector; and
    securing the replacement connector to the implanted lead.

13. The method of claim 12 wherein the step of securing the replacement connector comprises
    inserting a severed end of the implanted lead into both a rotatable housing on the replacement connector and a stationary housing on the replacement connector and
    displacing the rotatable housing with respect to the stationary housing.

14. The method of claim 13 wherein the step of making an electrical connection comprises sliding the severed end of the implanted lead onto a guide wire.

15. The method of claim 14 further comprising sealing the replacement connector to the severed end of the implanted lead to exclude body fluids.

16. The method according to claim 15 wherein the sealing step comprises
    enclosing the stationary housing and the rotatable housing in an elastomeric boot;
    placing a sealing means on the severed end of the lead, and
    connection the sealing means and the boot.

* * * * *